United States Patent [19]
Roduit et al.

[11] Patent Number: 5,922,870
[45] Date of Patent: Jul. 13, 1999

[54] PROCESS FOR THE PREPARATION OF ARYLAMIDES OF HETEROAROMATIC CARBOXYLIC ACIDS

[75] Inventors: Jean-Paul Roduit, Grône; Georges Kalbermatten, Ausserberg, both of Switzerland

[73] Assignee: Lonza AG, Gampel/Valais, Switzerland

[21] Appl. No.: 08/816,692

[22] Filed: Mar. 13, 1997

[30] Foreign Application Priority Data

Mar. 21, 1996 [CH] Switzerland ............... 0735/96

[51] Int. Cl.⁶ .......... C07C 69/76; C07D 239/24; C07D 241/10; C07D 213/56
[52] U.S. Cl. .......... 544/334; 544/335; 544/406; 544/408; 546/323; 564/161
[58] Field of Search .......... 564/161; 544/334, 544/335, 406, 408; 546/323

[56] References Cited

U.S. PATENT DOCUMENTS

| | | | |
|---|---|---|---|
| 4,128,554 | 12/1978 | Heck | 546/317 |
| 4,254,125 | 3/1981 | Sunder et al. | 514/253 |
| 4,618,366 | 10/1986 | Cramp et al. | 504/255 |
| 4,995,902 | 2/1991 | Brunner | 504/255 |
| 5,142,057 | 8/1992 | Suto et al. | 546/316 |
| 5,159,113 | 10/1992 | Nicholas | 564/132 |
| 5,166,352 | 11/1992 | Allphin | 546/314 |
| 5,288,866 | 2/1994 | Strong | 544/215 |
| 5,294,597 | 3/1994 | Foster et al. | 504/255 |
| 5,296,601 | 3/1994 | Suto et al. | 544/355 |
| 5,334,724 | 8/1994 | Kaufman et al. | 546/345 |
| 5,380,861 | 1/1995 | Scalone et al. | 546/323 |
| 5,534,635 | 7/1996 | Scalone et al. | 546/323 |
| 5,583,241 | 12/1996 | Spindler | 556/11 |
| 5,614,636 | 3/1997 | Roduit et al. | 546/327 |
| 5,676,267 | 10/1997 | Slat et al. | 215/12.1 |

FOREIGN PATENT DOCUMENTS

| | | |
|---|---|---|
| 0001187 | 3/1979 | European Pat. Off. |
| 0053011 | 6/1982 | European Pat. Off. |
| 0282658 | 3/1987 | European Pat. Off. |
| 0282266 | 9/1988 | European Pat. Off. |
| 0 353 187 | 1/1990 | European Pat. Off. |
| 0 582 825 | 2/1990 | European Pat. Off. |
| 0 488 474 | 6/1991 | European Pat. Off. |
| 0447004 | 9/1991 | European Pat. Off. |
| 0 461 401 | 11/1991 | European Pat. Off. |
| 0564406 | 10/1993 | European Pat. Off. |
| 0627422 | 5/1994 | European Pat. Off. |
| 0612758 | 8/1994 | European Pat. Off. |
| 0646590 | 9/1994 | European Pat. Off. |
| 0 673 932 | 9/1995 | European Pat. Off. |
| 42 07 604 | 10/1992 | Germany . |
| 0 664 754 | 3/1988 | Switzerland . |
| WO 94/27974 | 12/1994 | WIPO . |

OTHER PUBLICATIONS

Schoenberg, A., et al., J. Organ. Chem., vol. 39, No. 23, (1974), 3327–3331, (Schoenberg '331).
Takeuchi, Ryo, et al., J. Mol. Cat., vol. 66, No. 3 (1991), pp. 277–288, (Takeuchi '288).
Ben–David, Yehoshua et al., vol. II, No. 23, (1989), pp. 8742–8744, (Ben–David '744).
Patent Abstracts of Japan, vol. II, No. 369, (C–461), Dec. 2, 1987, (Japanese '461).
Testaferi, Lorenzo, et al., Tetrahedron, vol. 41, No. 7, (1985), pp. 1373–1384, (Testaferi).
Schoenberg et al., Journal of Organic Chemistry, vol. 39, No. 23, (1974), pp. 3327 to 3331.
Takeuchi et al., Journal of Molecular Catalysis, vol. 66, No. 3, (1991), pp. 277 to 288.
Ben–David et al., Journal of American Chemical Society, vol. 111, No. 23, (1989).
A. Togni et al., Inorg. Chim. Acta, (1994), 222, 213–224.
J. Org. Chem., (1980), 45, 4680.
J. Organometall. Chem., (1995), 503, 143–148.
Chemical Abstracts, (1988), vol. 109, 68849.
Shokubai Catalysis Society of Japan, 36, (1994), 580–584.
Chemical Abstracts, (1969), vol. 73, 130894.
Chemical Abstratcts, (1994), vol. 122, 187621.
Advanced Organic Chemistry, Mar., (1968), 21.
Chemical Abstracts, (1996), vol. 125, No. 3, 33323k.
Journal of Heterocyclic Chemistry, (1990), 27, 243.
Encyclopedia of Reagents for Organic Synthesis, (1995), 2769–2771.

Primary Examiner—Alan L. Rotman
Attorney, Agent, or Firm—Fisher, Christen & Sabol

[57] ABSTRACT

A process for the preparation of arylamides of heteroaromatic carboxylic acids of the formula:

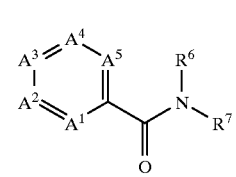

I in which each $A^n$ is nitrogen or $CR^n$ (n=1–5), with the proviso that at least one of the ring members is nitrogen and that two nitrogen atoms are not bonded directly to one another; $R^1$ to $R^5$, if present, independently of one another are hydrogen, $C_{1-4}$-alkyl or aryl, also one of the substituents $R^1$ to $R^5$ can be a group of the formula —OR, in which R is an optionally substituted aromatic or heteroaromatic radical; $R^6$ is hydrogen or $C_{1-4}$-alkyl; and $R^7$ is an optionally substituted aromatic or heteroaromatic radical. The amides are obtained from the corresponding heteroaromatic halogen compounds, the corresponding aromatic amines and carbon monoxide in the presence of a palladium diphosphine complex. Compounds of this class, especially those in which one of the substituents $R^1$ to $R^5$ is an aryloxy group, are important herbicides.

21 Claims, No Drawings

PROCESS FOR THE PREPARATION OF ARYLAMIDES OF HETEROAROMATIC CARBOXYLIC ACIDS

FIELD OF THE INVENTION

The invention relates to a process for the preparation of arylamides of heteroaromatic carboxylic acids by the reaction of heteroaromatic halogen compounds with carbon monoxide and aromatic amines in the presence of a catalyst and a base. It further relates to a novel intermediate for the process according to the invention.

The amides which can be prepared according to the invention have the general formula:

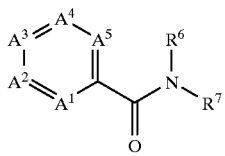

I in which:
- $A^1$ is nitrogen or $CR^1$,
- $A^2$ is nitrogen or $CR^2$,
- $A^3$ is nitrogen or $CR^3$,
- $A^4$ is nitrogen or $CR^4$ and
- $A^5$ is nitrogen or $CR^5$,
  - with the proviso that at least one of the ring members $A^1$ to $A^5$ is nitrogen and that two nitrogen atoms are not bonded directly to one another;
- $R^1$ to $R^5$, if present, independently of one another are hydrogen, $C_{1-4}$-alkyl or aryl, also one of the substituents $R^1$ to $R^5$ can be a group of the formula —OR, in which R is an optionally substituted aromatic or heteroaromatic radical;
- $R^6$ is hydrogen or $C_{1-4}$-alkyl; and
- $R^7$ is an optionally substituted aromatic or heteroaromatic radical.

These amides include especially the arylamides of pyridine-, pyrimidine-, pyrazine- and 1,3,5-triazine-carboxylic acids.

BACKGROUND ART

Numerous compounds of the structure of Formula I, especially those in which one of the substituents $R^1$ to $R^5$ is an aryloxy group (—OR) adjacent to a ring nitrogen atom, are important herbicides (International Published Patent Application No. WO 94/27974, European Published Patent Application No. 0,053,011, and European Published Patent Application No. 0,447,004).

These known compounds are conventionally synthesized from the corresponding carboxylic acids or carboxylic derivatives (acid chlorides, esters, and nitrites), although these are often difficult to obtain and consequently expensive.

BROAD DESCRIPTION OF THE INVENTION

The main object of the invention is to provide an alternative process which is based on more readily obtainable educts. Other objects and advantages of the invention are set out herein or are obvious herefrom to one skilled in the art.

The advantages and objects of the invention are achieved by the process and intermediates of the invention.

It has been found that halogen compounds of the general formula:

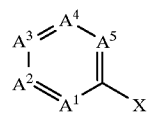

II in which $A^1$ to $A^5$ are as defined above and X is chlorine, bromine or iodine, react directly with carbon monoxide and a primary or secondary amine of the general formula:

$$R^6\text{—NH—}R^7$$

III in which $R^6$ and $R^7$ are as defined above, in the presence of a base, to give good to almost quantitative yields of the desired products (I) if a complex of palladium with a diphosphine of the general formula:

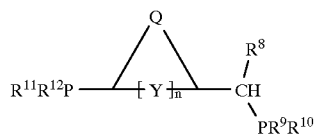

IV is present as a catalyst. In formula IV:
- $R^8$ is hydrogen or $C_{1-4}$-alkyl,
- $R^9$ to $R^{12}$ independently of one another are secondary or tertiary $C_{3-6}$-alkyl, $C_{5-7}$-cycloalkyl or optionally substituted phenyl,
- Y is $C^H{}_o$, $NH_p$ or oxygen,
- n is 0 or 1,
- o is 1 or 2,
- p is 0 or 1 and
- Q is a bridging organic radical which, together with the two adjacent carbon atoms and, if present (n=1), with Y forms an optionally substituted five-membered or six-membered saturated or aromatic carbocyclic or heterocyclic ring which, as an aromatic ring, can optionally be complexed with a transition metal.

Herein, $C_{1-4}$-alkyl are to be understood as meaning any linear or branched primary, secondary or tertiary alkyl groups having up to 4 carbon atoms, such as, methyl, ethyl, n-propyl, isopropyl, n-butyl, isobutyl or tertiary butyl.

Herein, aromatic or heteroaromatic radicals are to be understood as meaning especially monocyclic or polycyclic systems, such as, phenyl, naphthyl, biphenylyl, anthracenyl, furyl, pyrrolyl, pyrazolyl, thiophenyl, pyridyl, indolyl or quinolinyl. These radicals can carry one or more identical or different substituents, for example, halogens such as chloro, bromo or fluoro, lower alkyl groups such as methyl, halogenated alkyl groups such as trifluoromethyl, lower alkoxy groups such as methoxy, or lower alkylthio (alkanesulfanyl) or alkanesulfonyl groups such as methylthio or ethanesulfonyl.

Aromatic rings complexed with transition metals are to be understood as meaning especially $\eta^5$-cyclopentadienyl rings and $\eta^6$-benzene rings in sandwich and half-sandwich complexes such as metallocenes or related compounds, for example, in ferrocene or benzenechromium tricarbonyl.

The halogen compounds (II) used as starting materials are known compounds or can be prepared analogously to known compounds. Numerous compounds of this type have been published, for example, in U.S. Pat. No. 4,254,125 and European Published Patent Application No. 0,001,187.

The process according to the invention is preferentially suitable for the preparation of amides (I) in which $A^2$ is nitrogen and forms a pyridine ring with the remaining ring members. Amides (I) in which $R^1$ is a group of the formula —OR, R being as defined above, are particularly preferred.

Other preferred amides (I) are:
those in which $A^1$ is nitrogen and forms a pyridine ring with the remaining ring members,
those in which $A^1$ and $A^5$ are nitrogen and form a pyrimidine ring with the remaining ring members,
those in which $A^1$ and $A^4$ are nitrogen and form a pyrazine ring with the remaining ring members, and
those in which $A^1$, $A^3$ and $A^5$ are nitrogen and form a 1,3,5-triazine ring with the remaining ring members.

In the last four classes, those amides in which $R^2$ is a group of the formula —OR, R being as defined above, are in turn particularly preferred.

Of the amides (I) in which one of the substituents $R^1$ to $R^5$ is a group of the formula —OR, those in which R is an optionally substituted phenyl group are preferred. This applies especially to the above-mentioned amides containing an pyridine, pyrimidine, pyrazine or 1,3,5-triazine ring in which $R^1$ or $R^2$ is a group of the formula —OR.

Other preferred amides are those in which $R^6$ is hydrogen and $R^7$ is an optionally substituted phenyl group.

Preferred halogen compounds (II) are the chlorine compounds (X=Cl).

The diphosphines (IV) used are preferably those in which n=0 and Q, together with the two adjacent carbon atoms, forms a five-membered ring which is part of a ferrocene system. These compounds can be represented by the general formula:

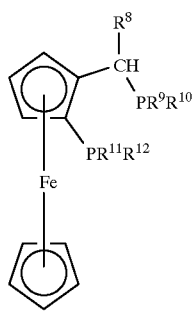

IVa in which $R^8$ to $R^{12}$ are as defined above, particularly preferred diphosphines being those in which $R^8$ is hydrogen or methyl. These compounds are chiral and have been used (especially when $R^8 \neq H$) as pure stereoisomers, for example, for asymmetric hydrogenations (see, e.g., European Published Patent Application No. 0,564,406, and European Published Patent Application No. 0,612,758). As no new elements of chirality are formed in the process according to the invention, these diphosphines can also be used here as racemates or other stereoisomeric mixtures. Very particularly preferred diphosphines (IVa) are those in which $R^9=R^{10}$ and $R^{11}=R^{12}$ and these substituents are selected from the group comprising isopropyl, tert-butyl, cyclohexyl and optionally substituted phenyl.

Other preferred diphosphines (IV) are those in which n=0 and Q, together with the two adjacent carbon atoms, forms a benzene, pyridine, pyrrole or furan ring.

Tricarbonyl-$\eta^6$-{1-(diphenylphosphino)-2-[1-(diphenylphosphino)ethyl]-benzene}chromium(0) may be mentioned here as an example (*J. Organometall. Chem.*, 1995, 503, 143–148).

Likewise, preferred diphosphines are those in which n=1, Y is a methylene group and Ý, together with Q and the two adjacent carbon atoms, forms a pyrrolidine ring which optionally carries further substituents. These diphosphines include, for example, (2S,4S)-1-tert-butoxycarbonyl-4-diphenylphosphino-2-(diphenylphosphinomethyl) pyrrolidine (BPPM) (*J. Org. Chem.*, 1980, 45, 4680).

The catalytically active palladium diphosphine complex is advantageously formed in situ by a process in which palladium in finely divided elemental form (e.g., palladium on activated charcoal), a Pd(II) salt (e.g., the chloride or the acetate) or a suitable Pd(II) complex [e.g., dichlorobis (triphenylphosphine)palladium(II)] is reacted with the diphosphine. The palladium is preferably used in an amount of 0.02 to 0.2 mol percent of Pd(II) or 0.5 to 2 mol percent of Pd(0) (as Pd/C), based in each case on the halogen compound (II). The diphosphine is advantageously used in excess (based on Pd), preferably in an amount of 0.2 to 5 mol percent, again based on the halogen compound (II).

The solvents used can be either relatively non-polar, for example toluene, xylene or methylcyclohexane, or polar, for example acetonitrile, tetrahydrofuran, N,N-dimethylacetamide or butyl acetate.

The base used is preferably a relatively weak base. The base does not need to be soluble in the solvent used. Examples of suitable bases are carbonates such as sodium carbonate or potassium carbonate, acetates such as sodium acetate, or secondary or tertiary phosphates such as dipotassium hydrogen phosphate or tripotassium phosphate. Particularly good results have been achieved with sodium carbonate or sodium acetate.

The reaction temperature is preferably 80° to 250° C.
The carbon monoxide pressure is preferably 1 to 50 bar.

DETAILED DESCRIPTION OF THE INVENTION

The following examples illustrate how the process according to the invention is carried out.

EXAMPLE 1

2-Chloro-6-[3-trifluoromethyl)phenoxy]pyridine 17.45 g (690 mmol) of sodium hydride (95 percent) was suspended in 420 ml of N,N-dimethylacetamide. 106.7 g (658 mmol) of 3-(trifluoromethyl)phenol was added dropwise over 2 hours at 15° C. The resultant phenate solution was added dropwise over 2.5 hours, under nitrogen, to a solution of 162.4 g (1.097 mol) of 2,6-dichloropyridine in 330 ml of N,N-dimethylacetamide, heated to 90° C. After a further 3 hours of reaction time, the mixture was cooled to room temperature, the precipitate of sodium chloride was filtered off and the filtrate was concentrated. The residue was taken up with toluene and 0.1 N hydrochloric acid, and the organic phase was washed with saturated sodium chloride solution and concentrated. The oily residue (ca. 200 g) was distilled under vacuum. The yield of the title compound was 151.5 g (84 percent) of a colorless oil, content (GC) 99.8 percent. Other data concerning the title compound was:

$n_D^{20}$=1.5267; MS; m/z: 273/275; 238; 39; $^1$H NMR (CDCl$_3$): δ=6.84 (d, J=7.8 Hz, 1H); 7.07 (d, J=7.8 Hz, 1H); 7.35 (m, 1H); 7.42 (m, 1H); 7.45–7.52 (m, 2H); 7.65 (t, J=7.8 Hz, 1H).

$^{13}$C NMR (CDCl$_3$): δ=109.88 (CH); 118.16 (CH); 119.24 (CH); 121.67 (CH); 123.74 (CF$_3$); 124.50 (CH); 130.24 (CH); 132.21 (CCF$_3$); 141.77 (CH); 149.12 (C); 153.89 (C); 162.28 (C).

EXAMPLE 2

3-Chloro-2-[3-(trifluoromethyl)phenoxy]pyridine 7.68 g of sodium hydride dispersion (ca. 50 percent in mineral oil) was washed with pentane under nitrogen and 100 ml of N,N-dimethylformamide was then added. 21.92 g (135 mmol) of 3-(trifluoromethyl)phenol was added dropwise over 30 minutes at room temperature. The resultant phenate solution was added dropwise over 2 hours, under nitrogen, to a solution of 20.1 g (136 mmol) of 2,3-dichloropyridine in 80 ml of N,N-dimethylformamide, heated to 120° C. After a reaction time of 3 hours, the mixture was cooled to room temperature, the precipitate of sodium chloride was filtered off and the filtrate was concentrated. The residue was extracted with toluene and 0.1 N hydrochloric acid and the organic phase was washed with saturated sodium chloride solution and concentrated. The oily residue was distilled under vacuum. The yield of the title compound was 24.75 g (67 percent) of a colorless oil, content (GC) 99.7 percent. Other data concerning the title compound was:

B.p.$_{18mbar}$=145°–148° C.; $n_D^{20}$=1.5282; MS; m/z: 273/275 $^1$H NMR (CDCl$_3$): δ=6.99 (m, 1H); 7.36 (d, 1H); 7.45–7.53 (m, 3H); 7.77 (d, 1H); 8.02 (d, 1H).

$^{13}$C NMR (CDCl$_3$): δ=118.66 (CH); 119.44 (C); 119.98 (CH); 121.75 (CH); 123.78 (CF$_3$); 124.94 (CH); 130.13 (CH); 132.16 (CCF$_3$); 139.65 (CH); 145.20 (CH); 153.88 (C); 158.51 (C).

EXAMPLE 3

N-(4-Fluorophenyl)-6-[3-(trifluoromethyl)phenoxy]pyridine-2-carboxamide 6.84 g (25 mmol) of 2-chloro-6-[3-trifluoromethyl)phenoxy]pyridine (content 99.5 percent, prepared according to Example 1), 4.17 g (37.5 mmol) of 4-fluoroaniline, 2.92 g (27.5 mmol) of sodium carbonate, 17.5 mg (25 μmol) of dichlorobis(triphenylphosphine)palladium(II) and 0.31 g (0.75 mmol) of(±)-1-[2-(diphenylphosphino)ferrocenyl] ethyldiphenylphosphine (IVa, R$^8$=methyl, R$^9$=R$^{10}$=R$^{11}$=R$^{12}$=phenyl, prepared according to A. Togni et al., *Inorg. Chim. Acta*, 1994, 222, 213–224) in 25 ml of xylene were placed in an autoclave at room temperature. The autoclave was flushed with inert gas, carbon monoxide was then introduced under a pressure of 5 bar and the temperature was raised to 200° C. The CO pressure was increased to 16 bar and the mixture was stirred for 21 hours at 200° C. After cooling to room temperature and depressurization, the reaction mixture was treated with 50 ml of xylene and 50 ml of water and filtered. The aqueous phase was extracted with 25 ml of xylene and the combined organic phases was washed with 30 ml of water. The composition of the dissolved products was determined by GC. 97.8 percent of the title compound (amide) and 2.2 percent of by-product (secondary amine formed by direct substitution of Cl by the aniline) were found. After distillation of the solvent, the crude product was obtained in the form of a yellow solid. The crude yield (HPLC analysis, with standard) of the title product was 89.9 percent. The crude product was purified by recrystallization from methylcyclohexane. The yield of the title compound was 6.3 g (67 percent) of colorless crystals. Other data concerning the title compound was:

M.p: 104°–105° C.; MS; m/z: 376 (M$^+$), 238 $^1$H NMR (CDCl$_3$): δ=6.99–7.04 (m, 2H); 7.17 (d, J=8.4 Hz, 1H); 7.40 (m, 1H); 7.46–7.51 (m, 2H); 7.55–7.63 (m, 3H); 7.93 (t, J=7.8 Hz, 1H); 8.03 (d, J=7.8 Hz, 1H); 9.24 (br. m, 1H).

EXAMPLE 4

N-(4-Fluorophenyl)-6-[3-trifluoromethyl)phenoxy]pyridine-2-carboxamide

The procedure was as described in Example 3 except that the (±)-1-[2-(diphenylphosphino)ferrocenyl] ethyldiphenylphosphine was replaced with the same molar amount of (±)-1-[2-(diphenylphosphino)ferrocenyl]ethyl-di-tert-butylphosphine (IVa, R$^8$=methyl, R$^9$=R$^{10}$=tert-butyl, R$^{11}$=R$^{12}$=phenyl). The CO pressure was 19 bar. The composition of the dissolved products in the xylene phase was determined by GC. 97.2 percent of the title compound (amide) and 2.8 percent of by-product (secondary amine) were found.

EXAMPLE 5

N-(4-Fluorophenyl)-6-[3-(trifluoromethyl)phenoxy]pyridine-2-carboxamide

The procedure was as described in Example 3 except that the (±)-1-[2(diphenylphosphino)ferrocenyl] ethyldiphenylphosphine was replaced with the same molar amount of (±)-1-[2-(diphenylphosphino)ferrocenyl]-ethyldiisopropylphosphine (IVa, R$^8$=methyl, R$^9$=R$^{10}$=isopropyl, R$^{11}$=R$^{12}$=phenyl). The CO pressure was 19 bar. The composition of the dissolved products in the xylene phase was determined by GC. 96.7 percent of the title compound (amide) and 3.3 percent of by-product (secondary amine) were found.

EXAMPLE 6

N-(4-Fluorophenyl)-6-[3-(trifluoromethyl)phenoxy]pyridine-2-carboxamide

The procedure was as described in Example 3 except that the (±)-1-[2-(diphenylphosphino)ferrocenyl] ethyldiphenylphosphine was replaced with the same molar amount of (±)-1-[2-(diisopropylphosphino)ferrocenyl]ethyl-di-tert-butylphosphine (IVa, R$^8$=methyl, R$^9$=R$^{10}$=tert-butyl, R$^{11}$=R$^{12}$=isopropyl). The CO pressure was 19 bar. The composition of the dissolved products in the xylene phase was determined by GC. 98.9 percent of the title compound (amide) and 1.1 percent of by-product (secondary amine) were found.

EXAMPLE 7

N-(4-Fluorophenyl)-6-[3-(trifluoromethyl)phenoxy]pyridine-2-carboxamide

The procedure was as in Example 4 except that the sodium carbonate was replaced with the same molar amount of sodium acetate as the base. The CO pressure was 19 bar. The composition of the dissolved products in the xylene phase was determined by GC. 99.7 percent of the title compound (amide), 0.2 percent of educt and <0.1 percent of by-product (secondary amine) were found.

EXAMPLE 8

N-(4-Fluorophenyl)-6-[3-(trifluoromethyl)phenoxy]pyridine-2-carboxamide

The procedure was as in Example 4 except that the dichlorobis(triphenylphosphine)palladium(II) was replaced with the same molar amount of palladium(II) chloride. The CO pressure was 19 bar. The composition of the dissolved products in the xylene phase was determined by GC. 96.7 percent of the title compound (amide) and 3.3 percent of by-product (secondary amine) were found.

EXAMPLE 9

N-(4-Fluorophenyl)-6-[3-(trifluoromethyl)phenoxy]pyridine-2-carboxamide

The procedure was as in Example 4 except that the dichlorobis(triphenylphosphine)palladium(II) was replaced with the same molar amount of palladium(II) acetate. The CO pressure was 19 bar. The composition of the dissolved products in the xylene phase was determined by GC. 99.0 percent of the title compound (amide) and 0.8 percent of by-product (2-[3-(trifluoromethyl)phenoxy]pyridine formed by hydrogenolysis of the chloride) were found.

EXAMPLE 10

N-(4-Fluorophenyl)-6-[3-(trifluoromethyl)phenoxy]pyridine-2-carboxamide

The procedure was as in Example 3 except that the ferrocenylphosphine was replaced with 0.21 g (0.75 mmol) of (2S,4S)-1-tert-butoxycarbonyl-4-(diphenylphosphino)-2-(diphenylphosphinomethyl)pyrrolidine (Fluka). The reaction time was 20 hours and the CO pressure was 17 bar. The composition of the dissolved products in the xylene phase was determined by GC. 98.7 percent of the title compound (amide) and 1.1 percent of by-product (secondary amine) were found.

EXAMPLE 11

N-(4-Fluorophenyl)-6-[3-(trifluoromethyl)phenoxy]pyridine-2-carboxamide

The procedure was as in Example 4 except that only 75 μmol of (±)-1-[2-(diphenylphosphino)ferrocenyl]ethyl-di-tert-butylphosphine was used. The CO pressure was 19 bar. The composition of the dissolved products in the xylene phase was determined by GC. 88.8 percent of the title compound (amide), 7.4 percent of unconverted educt and 3.3 percent of by-product (secondary amine) were found.

EXAMPLE 12

N-(4-Fluorophenyl)-6-[3-(trifluoromethyl)phenoxy]pyridine-2-carboxamide

The procedure was as in Example 4 except that only 27.5 mmol of 4-fluoroaniline was used. The CO pressure was 19 bar. The composition of the dissolved products in the xylene phase was determined by GC. 97.3 percent of the title compound (amide) and 2.7 percent of by-product (secondary amine) were found.

EXAMPLE 13

N-(4-Fluorophenyl)-6-[3-(trifluoromethyl)phenoxy]pyridine-2-carboxamide 6.84 g (25 mmol) of 2-chloro-6-[3-(trifluoromethyl)phenoxy]pyridine (content 99.5 percent, prepared according to Example 1), 3.33 g (30 mmol) of 4-fluoroaniline, 2.92 g (27.5 mmol) of sodium carbonate, 2.8 mg (12.5 μmol) of palladium(II) acetate and 68 mg (125 μmol) of (±)-1-[2-(diphenylphosphino)ferrocenyl]ethyl-di-tert-butylphosphine (IVa, $R^8$=methyl, $R^9$=$R^{10}$=tert-butyl, $R^{11}$=$R^{12}$=phenyl) in 25 ml of acetonitrile were placed in an autoclave at room temperature. The autoclave was flushed with inert gas, carbon monoxide was then introduced under a pressure of 5 bar and the temperature was raised to 150° C., the pressure increasing to 7.6 bar. The mixture was stirred for 4 hours at 150° C. After cooling to room temperature and depressurization, the solvent was distilled off and the residue was taken up at 80° C. with 90 ml of methylcyclohexane. The resultant suspension was filtered and the filter cake was rinsed with 10 ml of warm methylcyclohexane. The product crystallized out when the filtrate was cooled to 5° C. The yield of the title compound was 8.11 g (86.2 percent) of a light beige solid. The melting point of the title compound was 104.5°–105.2° C.

EXAMPLE 14

N-(2,4-Difluorophenyl)-2-[3-(trifluoromethyl)phenoxy]pyridine-3-carboxamide (Diflufenicam)

Analogously to Example 3, 6.84 g (25 mmol) of 3-chloro-2-(3-trifluoromethyl)phenoxypyridine (prepared according to Example 2), 4.84 g (37.5 mmol) of 2,4-difluoroaniline, 2.92 g (27.5 mmol) of sodium carbonate, 17.5 mg (25 μmol) of dichlorobis(triphenylphosphine)palladium(II) and 0.31 g (0.75 mmol) of (±)-1-[2-(diphenylphosphino)ferrocenyl]ethyl-di-tert-butylphosphine in 25 ml of xylene were reacted under a CO pressure of 15 bar at 150° C. for 19 hours. The conversion was ca. 70 percent. The mixture was worked up as in Example 3 to give 6 g of crude product in the form of a yellow crystalline solid. It was purified by recrystallization from 50 ml of methylcyclohexane. The yield of the title compound was 3.25 g (33 percent) of a white solid. Other data concerning the title compound was:

M.p.: 157°–159° C.; MS; m/z: 394 ($M^+$), 266 (100 percent) $^1$H NMR (CDCl$_3$): δ=6.89–6.96 (m, 2H); 7.26 (m, 1H); 7.46 (m, 1H); 7.54–7.63 (m, 3H); 8.28 (dd, 1H); 8.52 (m, 1H); 8.71 (dd, 1H); 9.97 (br. s, 1H).

EXAMPLE 15

N-(4-Fluorophenyl)-6-[3-(trifluoromethyl)phenoxy]pyrazine-2-carboxamide

Analogously to Example 3, 25 mmol of 2-chloro-6-[3-(trifluoromethyl)phenoxy]pyrazine (prepared according to U.S. Pat. No. 4,254,125, Example 21), 27.5 mmol of 4-fluoroaniline, 2.92 g (27.5 mmol) of sodium carbonate, 17.5 mg (25 μmol) of dichlorobis(triphenylphosphine)palladium(II) and 0.31 g (0.75 mmol) of (±)-1-[2-(diphenylphosphino)-ferrocenyl]ethyl-di-tert-butylphosphine in 25 ml of xylene were reacted under a CO pressure of 17 bar at 120° C. for 21 hours. The composition of the dissolved products in the xylene phase was determined by GC. 65.3 percent of the title compound (amide) and 34.7 percent of by-product (secondary amine) were found. The amide was isolated by column chromatography and purified. Data concerning the title product was:

M.p.: 109°–110° C., colorless solid $^1$H NMR (CDCl$_3$): δ=7.02–7.05 (m, 2H); 7.43 (m, 1H); 7.48–7.53 (m, 2H); 7.58–7.65 (m, 3H); 8.67 (s, 1H); 8.94 (br. s, 1H); 9.22 (s, 1H).

COMPARATIVE EXAMPLE 1

The procedure was as described in Example 3 except that the (±)-1-[2-(diphenylphosphino)ferrocenyl]ethyldiphenylphosphine was replaced with the same molar amount of triphenylphosphine. After a reaction time of 15.5 hours at a CO pressure of 15 bar, the composition of the dissolved products in the xylene phase was determined by GC. Only 43.2 percent of the desired product and 56.8 percent of unconverted educt were found.

COMPARATIVE EXAMPLE 2

The procedure was as described in Example 3 except that the (±)-1-[2-(diphenylphosphino)ferrocenyl]ethyldiphenylphosphine was replaced with the same molar amount of tri-n-butylphosphine. After a reaction time of 15 hours at a CO pressure of 14 bar, the composition of the dissolved products in the xylene phase was determined by GC. Only traces (0.4 percent) of the desired product and 96.8 percent of unconverted educt were found.

COMPARATIVE EXAMPLE 3

The procedure was as described in Example 3 except that the (±)-1-[2-(diphenylphosphino)ferrocenyl]

ethyldiphenylphosphine was replaced with the same molar amount of 1,2-bis(diphenylphosphino)ethane. After a reaction time of 20.2 hours at a CO pressure of 14.7 bar, the composition of the dissolved products in the xylene phase was determined by GC. Only traces (2.2 percent) of the desired product and 97.7 percent of unconverted educt were found.

What is claimed is:

1. A process for the preparation of an amide of the formula:

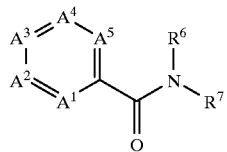

I wherein:
$A^1$ is nitrogen or $CR^1$,
$A^2$ is nitrogen or $CR^2$,
$A^3$ is nitrogen or $CR^3$,
$A^4$ is nitrogen or $CR^4$, and
$A^5$ is nitrogen or $CR^5$,
  with the proviso that at least one of the ring members $A^1$ to $A^5$ is nitrogen and that two nitrogen atoms are not bonded directly to one another;
$R^1$ to $R^5$, if present, independently of one another are hydrogen, $C_{1-4}$-alkyl or aryl, also one of the substituents $R^1$ to $R^5$ can be a group of the formula —OR, in which R is an optionally substituted aromatic or heteroaromatic radical;
$R^6$ is hydrogen or $C_{1-4}$-alkyl; and
$R^7$ is an optionally substituted aromatic or heteroaromatic radical, comprising reacting a halogen compound of the formula:

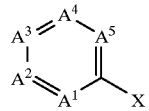

II wherein $A^1$ to $A^5$ are as defined above and X is chlorine, bromine or iodine, with carbon monoxide and a primary or secondary amine of the formula:

$R^6$—NH—$R^7$   III wherein $R^6$ and $R^7$ are as defined above, in the presence of a complex of palladium with a diphosphine of the formula:

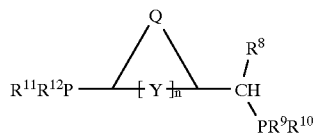

IV wherein:
$R^8$ is hydrogen or $C_{1-4}$-alkyl, $R^9$ to $R^{12}$ independently of one another are secondary or tertiary $C_{3-6}$-alkyl,
$C_{5-7}$-cycloalkyl or optionally substituted phenyl,
Y is $CH_o$, $NH_p$ or oxygen,
n is 0 or 1,
o is 1 or 2,
p is 0 or 1 and
Q is a bridging organic radical which, together with the two adjacent carbon atoms and, if present, with Y forms an optionally substituted five-member or six-member saturated or aromatic carbocyclic or heterocyclic ring which, as an aromatic ring, can optionally be complexed with a transition metal, and with a base other than said primary or secondary amine.

2. The process according to claim 1, wherein $A^2$ is nitrogen and part of a pyridine ring.

3. The process according to claim 2, wherein $R^1$ is a group of the formula —OR, R being as defined in claim 1.

4. The process according to claim 1, wherein $A^1$ is nitrogen and part of a pyridine ring.

5. The process according to claim 1, wherein $A^1$ and $A^5$ are nitrogen and part of a pyrimidine ring.

6. The process according to claim 1, wherein $A^1$ and $A^4$ are nitrogen and part of a pyrazine ring.

7. The process according to claim 1, wherein $A^1$, $A^3$ and $A^5$ are nitrogen.

8. The process according to claim 1, wherein $R^1$ is a group of the formula —OR, R being as defined in claim 1.

9. The process according to claim 4, wherein $R^2$ is a group of the formula —OR, R being as defined in claim 1.

10. The process according to claim 5, wherein $R^2$ is a group of the formula —OR, R being as defined in claim 1.

11. The process according to claim 6, wherein $R^2$ is a group of the formula —OR, R being as defined in claim 1.

12. The process according to claim 7, wherein $R^2$ is a group of the formula —OR, R being as defined in claim 1.

13. The process according to claim 3, wherein R is an optionally substituted phenyl group.

14. The process according to claim 13, wherein $R^6$ is hydrogen and $R^7$ is an optionally substituted phenyl group.

15. The process according to claim 14, wherein X is chlorine.

16. The process according to claim 12, wherein R is an optionally substituted phenyl group.

17. The process according to claim 16, wherein $R^6$ is hydrogen and $R^7$ is an optionally substituted phenyl group.

18. The process according to claim 17, wherein X is chlorine.

19. The process according to claim 1, wherein the base is a carbonate or an acetate.

20. The process according to claim 1, wherein, in said diphosphine of formula IV, n=0, and Q, together with the two adjacent carbon atoms, forms a benzene, pyridine, pyrrole or furan ring.

21. The process according to claim 1, wherein, in said diphosphine of formula IV, n=1, Y is a methylene group, and Y, together with Q and the two adjacent carbon atoms, forms a pyrrolidine ring which can optionally have further substituents.

* * * * *